(12) United States Patent
Barton et al.

(10) Patent No.: US 7,169,490 B2
(45) Date of Patent: Jan. 30, 2007

(54) HYDROGEN CONCENTRATION SENSOR FOR AN ELECTROCHEMICAL FUEL CELL

(75) Inventors: Russell H Barton, New Westminster (CA); Michael P Sexsmith, North Vancouver (CA)

(73) Assignee: Ballard Power Systems Inc., Burnaby (CA)

( * ) Notice: Subject to any disclaimer, the term of this patent is extended or adjusted under 35 U.S.C. 154(b) by 320 days.

(21) Appl. No.: 10/811,791

(22) Filed: Mar. 29, 2004

(65) Prior Publication Data

US 2005/0214603 A1 Sep. 29, 2005

(51) Int. Cl.
*H01M 8/00* (2006.01)
*H01M 8/04* (2006.01)

(52) U.S. Cl. .............................. 429/13; 429/12; 429/22; 429/24

(58) Field of Classification Search ................... 429/22, 429/24, 12, 13
See application file for complete search history.

(56) References Cited

U.S. PATENT DOCUMENTS

| | | | |
|---|---|---|---|
| 4,280,183 A | 7/1981 | Santi | 364/497 |
| 4,662,212 A | 5/1987 | Noguchi et al. | 73/24 |
| 6,242,120 B1 * | 6/2001 | Herron | 429/22 |
| 6,455,181 B1 | 9/2002 | Hallum | 429/13 |
| 6,541,141 B1 | 4/2003 | Frank et al. | 429/17 |
| 2002/0110713 A1 | 8/2002 | Reindl et al. | 429/22 |

FOREIGN PATENT DOCUMENTS

| | | |
|---|---|---|
| EP | 0 174 627 B1 | 6/1993 |
| GB | 727891 | 4/1955 |
| GB | 2 210 977 A | 6/1989 |
| GB | 2 257 255 A | 1/1993 |
| WO | WO 02/31488 A1 | 4/2002 |

* cited by examiner

*Primary Examiner*—Patrick Joseph Ryan
*Assistant Examiner*—Thomas H. Parsons
(74) *Attorney, Agent, or Firm*—Seed IP Law Group PLLC

(57) ABSTRACT

In a hydrogen gas line where the composition of the gas is primarily hydrogen, impurities present in the gas line will typically reduce the speed of sound. Accordingly, an acoustic sensor can be used in such a hydrogen gas line to indicate when impurities have accumulated in the gas line. In particular, the hydrogen gas line may be in a fuel line for an electrochemical fuel cell system. The sensor may comprise transducers, more particularly piezoelectric transducers, as both sound detectors and/or sound generators. Further, the sensor can measure either the speed or frequency of sound to determine the hydrogen concentration. If the fuel is recirculated back to the anode inlet, such a hydrogen sensor in the anode exhaust may be used to determine when it is beneficial to purge the anode exhaust to the external atmosphere.

15 Claims, 1 Drawing Sheet

HYDROGEN CONCENTRATION SENSOR FOR AN ELECTROCHEMICAL FUEL CELL

BACKGROUND OF THE INVENTION

1. Field of the Invention

The present invention relates to a fuel cell combined with an improved hydrogen gas sensor. In particular, the improved hydrogen gas sensor may be employed to measure a hydrogen concentration in an anode exhaust passage within an electrochemical fuel cell.

2. Description of the Related Art

Electrochemical fuel cells convert reactants, namely fuel and oxidant fluid streams, to generate electric power and reaction products. Electrochemical fuel cells generally employ an electrolyte disposed between two electrodes, namely a cathode and an anode. The electrodes each comprise an electrocatalyst disposed at the interface between the electrolyte and the electrodes to induce the desired electrochemical reactions.

The fuel fluid stream supplied to a fuel cell anode typically comprises hydrogen, which may be, for example, substantially pure hydrogen, or a dilute hydrogen stream such as a reformate stream. Further, the hydrogen exhaust, or a portion thereof, may be recirculated back to the fuel cell. The oxidant fluid stream supplied to a fuel cell cathode typically comprises oxygen, which may be, for example, substantially pure oxygen, or a dilute oxygen stream such as air.

At the cathode, oxygen in the air is consumed by the electrochemical process and a small amount of oxygen diffuses through the membrane to the anode. The oxygen concentration at the cathode flow field inlet is about 21% and may typically be about 10% at the oxidant flow field outlet. The average concentration of nitrogen from the inlet to the outlet of the cathode flow field is thus about 85%. The nitrogen diffuses through the membrane to the anode and if allowed to equilibrate, the nitrogen concentration at the anode would be essentially the same as at the cathode, about 80–85%. In operation, this results in nitrogen concentration in the recycle loop increasing until the partial pressure of nitrogen is nearly the same on both the anode and cathode sides of the membrane. U.S. Pat. No. 6,541,141 discloses periodically, for example every five minutes, purging the anode side to prevent the build-up of nitrogen gas.

In a fuel cell, gas sensors, such as hydrogen sensors may be used to monitor the hydrogen concentration in the fuel streams. Instead of simply periodically purging the anode exhaust stream periodically, the anode exhaust could be purged as a result of a measured hydrogen concentration falling below a threshold value. Further, hydrogen concentration may be used as an indicator of the fuel cell performance and operating efficiency. For example, if there is an excessive amount of hydrogen in the fuel stream exhausted from the fuel cell, it may indicate poor operating efficiency. U.S. Patent Application No. 2002/0110713(now U.S. Pat. No. 6,852,434), which is hereby incorporated by reference in its entirety, discloses the use of a gas sensor in the interior fluid passages within a fuel cell assembly or within fluid passages employed to transport reactant fluid streams to or from the fuel cell(s).

The present fuel cell assembly incorporates an improved hydrogen sensor that operates reliably and accurately when located in a fuel fluid stream passage within an electrochemical fuel cell.

BRIEF SUMMARY OF THE INVENTION

The speed of sound in a gas is dependent on the composition of the gas itself and more particularly on the molecular mass of the gas. In a hydrogen gas line where the composition of the gas is primarily hydrogen, impurities present in the gas line will typically reduce the speed of sound. In an embodiment, a fuel cell assembly comprises: at least one fuel cell comprising: an anode and a cathode, each having an inlet and an exhaust; an electrolyte interposed between the anode and the cathode; a fuel passage in fluid communication with the anode for directing a fuel stream to and from the anode; an oxidant passage in fluid communication with the cathode for directing an oxidant stream to and from the cathode. The fuel cell assembly also comprises a gas sensor operably associated with the fuel passage for measuring the concentration of hydrogen gas in the fuel stream, the sensor comprising a sound generator and a sound detector.

The sound generator and sound detector may be individually or collectively transducers, particularly piezoelectric transducers. A temperature sensor may also be associated with the gas sensor to correct for temperature in calculating the hydrogen concentration.

In an embodiment, the fuel cell assembly recirculates the fuel line from the anode exhaust back to the anode inlet. In such an embodiment, it may be desirable to measure the hydrogen gas concentration in the anode exhaust passage and then purge the hydrogen to the external atmosphere when the measured hydrogen concentration falls below a predetermined threshold. Accordingly, a method of operating an electrochemical fuel cell system having a cathode and an anode may comprise:

(a) directing an oxidant stream to and from the cathode;
(b) directing a hydrogen stream to and from the anode;
(c) determining the concentration of hydrogen in the hydrogen stream by: generating a sound in the fuel stream passage; measuring an acoustic property of the sound; and calculating the hydrogen concentration based on the measured acoustic property.

The acoustic property may be, for example, the speed or the frequency of sound.

More generally, an embodiment comprises a method of determining the concentration of hydrogen in a hydrogen gas line. In this embodiment, the method comprises generating a sound in the hydrogen gas line; measuring an acoustic property of the sound; and calculating the hydrogen concentration based on the measured acoustic property.

These and other aspects of the invention will be evident upon reference to the attached figures and following detailed description.

BRIEF DESCRIPTION OF THE DRAWINGS

In the above figures, similar references are used in different figures to refer to similar elements.

DETAILED DESCRIPTION OF THE INVENTION

The speed of sound in an ideal gas is given by the relationship:

$$v^2 = \gamma RT/M \tag{1}$$

where v is the speed of sound; γ is the adiabatic constant; R is the general gas constant (8.314 J/mol K); T is the absolute temperature; and M is the molecular mass of the gas in kg/mol. The adiabatic constant γ is the ratio of the specific heat of the gas at constant pressure to the specific heat of the gas at constant volume ($C_p/C_v$). For diatomic molecules like $H_2$ and $N_2$, γ=1.4 and for polyatomic molecules, γ=4/3.

In a typical fuel cell environment, the gases present are $H_2$, $N_2$, $O_2$ and $H_2O$. Table 1 provides the molecular masses of these gases with their corresponding speed of sound at 25° C. The principle source of variation between the speeds of sound between the gases arises from the different molecular masses of the gas. Differences in the adiabatic constant between gases is relatively small and thus a mixture of gases has a velocity that can be approximated to the weighted average of the velocities of the pure gases.

TABLE 1

| | Molecular mass | Speed of sound |
|---|---|---|
| $H_2$ | 2.016 g/mol | 1284 m/s |
| $N_2$ | 28.0134 g/mol | 334 m/s |
| $O_2$ | 31.9988 g/mol | 316 m/s |
| $H_2O$ | 18.015 g/mol | 494 m/s |

The relationship between the speed of sound and the composition of gases that make up a mixture as in equation 1 has been used in gas sensors, primarily to measure carbon dioxide concentration in an air sample. See for example, WO 02/31488; U.S. Pat. No. 4,280,183; U.S. Pat. No. 4,662,212; GB 2,257,255 and GB 2,210,977 all herein incorporated by reference in their entireties.

Figure 1:
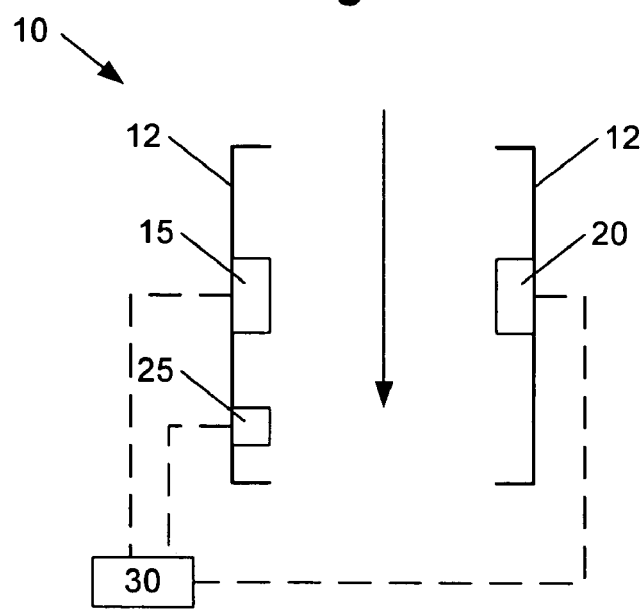
FIG. 1 is a cross-sectional schematic of an acoustic gas sensor.

FIG. 1 is a schematic of a representative acoustic gas sensor 10. A housing 12 is illustrated as a cross-section of, for example, a tube or pipe through which a gas may flow, represented by the arrow in FIG. 1. A suitable acoustic gas sensor 10 may comprise two ultrasonic transducers, a transmitting transducer 15 and a receiving transducer 20, positioned in housing 12 and driven by electronic signals, either continuously or in bursts. The transducers 15, 20 are mounted in housing 12 so as to be in the gas to be monitored and positioned a predetermined distance apart, for example 20 cm. A temperature sensor 25, comprising for example, a thermistor, a temperature measuring resistor or a thermocouple, may also be present to measure the temperature of the gas in housing 12. The resulting temperature data may be used to eliminate the temperature dependence of the velocity of sound in the gas. Controller 30 is in communication with transducer 15, 20, and temperature sensor 25, and measures the concentration of hydrogen in the gas.

Transducers 15, 20 may, for example, consist of thin plates of a piezoelectric material (e.g., lead zirconate-titanate) with metal depositions. It may be advantageous to operate in the ultrasonic frequency range and electroacoustic elements operating in frequencies from 30 kHz to 1 MHz are commercially available. Since the piezoelectric effect is reversible, the same type of electroacoustic element may be used as both transmitters and receivers. In addition to piezoelectric transducers, electrostatic/capacitive drive/detection can be used, as well as magnetostrictive transducers.

If a burst of sound is generated, a measurement of the time for its propagation through the gas provides an easy calculation of the gas velocity as the distance between transmitting and receiving transducers is known. For a length of 20 cm, the measured time in pure hydrogen gas would be 0.00015 seconds. With a clock speed of only 1 MHz, this represents 155 cycles so even a moderately fast CPU can measure the relevant times to a high degree of accuracy.

If a continuous acoustic wave is generated, the transducers may be frequency determining elements in a free running oscillator. The oscillation frequency is influenced by the transit time for the acoustic waves between transmitting transducer and receiving transducer. Since the distance is constant, the frequency will be dependent on the sound velocity.

Such acoustic gas sensors are particularly useful in binary gas systems where the speed of sound is only dependent on the two gases present. When 3 or more gases are present, a change in concentration of one of the gases may be, at least partially, masked by a change in concentration of another gas. This may not be a significant problem when measuring hydrogen concentration in a hydrogen gas line. The speed of sound in hydrogen gas is relatively fast and the presence of any impurity (for example, nitrogen, oxygen, water, carbon dioxide, etc.) therein will serve to reduce the speed of sound. The accuracy of the measurement may be affected by the species of impurity present but this may not be significant for many applications, such as in an electrochemical fuel cell system.

Figure 2:
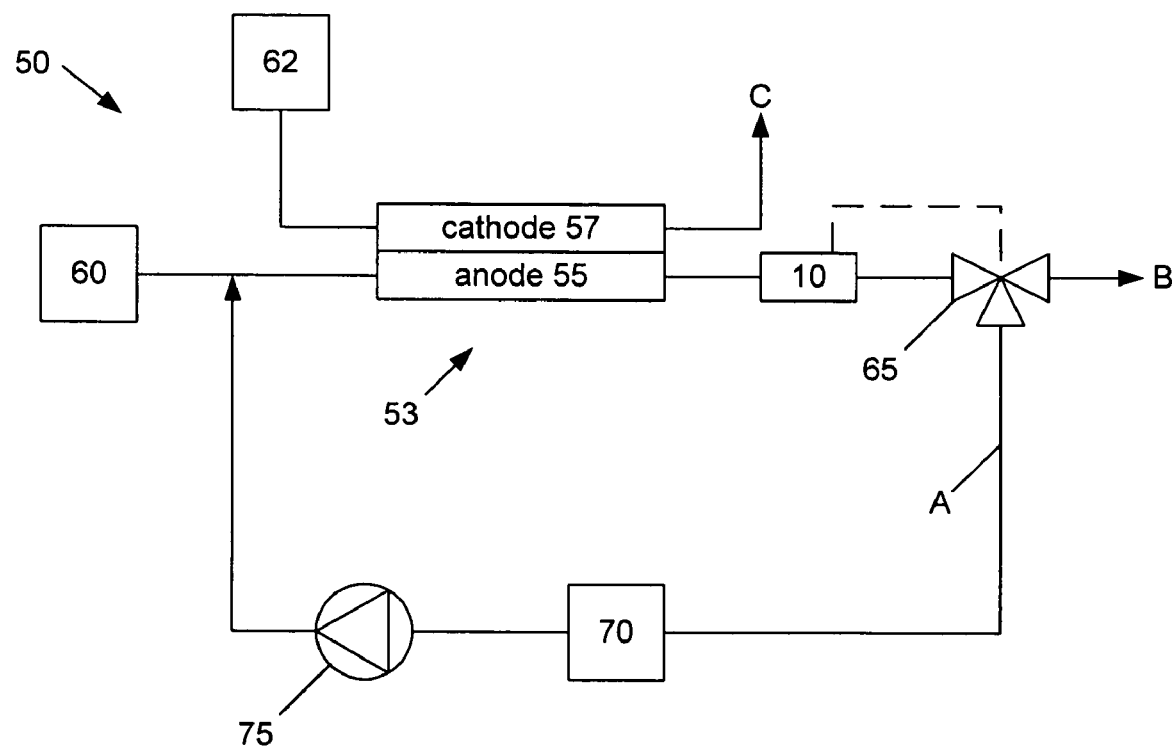
FIG. 2 is a schematic of an electrochemical fuel cell system with a hydrogen sensor in the fuel cell exhaust.

FIG. 2 is a schematic of a fuel cell system 50 comprising a fuel cell stack 53. Fuel cell stack 53 may comprise a single fuel cell, or more commonly a plurality of fuel cells connected in series. Each fuel cell comprises an anode 55 and a cathode 57.

Hydrogen originates from a hydrogen source 60 and is directed to anode 55. Hydrogen source 60 may be, for example, a hydrogen tank such as a pressurized tank or a metal hydride storage tank. Alternatively, the hydrogen may originate from a gas generation system or fuel processing system which produces a hydrogen-rich gas through reforming. In such a case, a suitable purification system (not shown) may be interposed between the reformer and anode 55 to remove from the hydrogen stream substances that cannot be consumed by fuel cell 53 (for example $CO_2$, residues of the reformer, inert gases, etc.). Although not shown in FIG. 2, another gas sensor 10 may be interposed at the hydrogen inlet, particularly when a fuel processing system is used to ensure that adequate hydrogen is being supplied to fuel cell stack 53.

The oxidant originates from an oxidant source 62 and is directed to cathode 57. Oxidant source 62 may be, for example, a compressed oxygen tank or more commonly, a dilute oxidant stream such as air. The oxidant stream may also be recirculated through cathode 57, however when the oxidant stream is a dilute oxidant stream such as air, the oxidant stream is typically discarded after it has passed once through the fuel cell stack as illustrated in FIG. 2 as oxidant exhaust path C. A humidifier (not shown) may also be used with either or both the oxidant and hydrogen streams.

The ratio of hydrogen supplied to anode 55 to the amount of hydrogen consumed at anode 55 is referred to as the stoichiometric ratio. A stoichiometric ratio grater than 1, for example, 1.2 to 5.0 and more preferably 1.5 to 2.0, makes it possible to recirculate the hydrogen gas.

An acoustic gas sensor 10 as described above with respect to FIG. 1, measures the hydrogen concentration at the anode exhaust and is located before purge valve 65. Under normal operation, when the concentration of hydrogen in the exhaust is at an acceptable level for recirculation, purge valve 65 directs the hydrogen stream from the anode exhaust back to the anode inlet by way of the recirculation loop A. However, when gas sensor 10 indicates that the hydrogen concentration in the anode exhaust has fallen below a predetermined value, purge valve 65 may purge the anode exhaust line by directing the hydrogen stream to the external atmosphere as shown by hydrogen exhaust path B. The dashed line between gas sensor 10 and purge valve 65 indicates that purge valve 65 is controlled by the concentration of hydrogen present in the anode exhaust as measured by gas sensor 10.

In electrochemical fuel cell system 50, it is not necessary to accurately measure the hydrogen concentration in the anode exhaust. Gas sensor 10 only provides some additional control as to when it is appropriate to purge the anode exhaust and ensure that there is adequate hydrogen in fuel cell stack 53 to ensure optimal operation and avoid, for example, fuel starvation. Further, the operating temperature of fuel cell stack 53 may be kept relatively constant, typically between 60 and 80° C. such that gas sensor 10 may not need a temperature sensor 25 as shown in FIG. 1.

The recirculation loop A may also comprise a liquid separator 70 and a recirculation device 75. Recirculation device 75 may be, for example, a fan and may be used to increase the pressure of the recirculated exhaust stream to compensate for the pressure drop across anode 55, the subsequent line elements and liquid separator 70. Liquid separator 70 may be used to remove excess product water generated by fuel cell 53. Excess water extracted from liquid separator 70 or from the reactant exhaust (not shown), can be accumulated and recirculated and used as a source of coolant fluid or humidification water, or simply drained from the system. In a different embodiment, the recirculated fuel stream may be merged directly with the incoming fresh fuel stream, thereby humidifying the incoming fresh reactant stream and avoiding the need for a separate humidifier.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A fuel cell assembly comprising:
   at least one fuel cell comprising:
   an anode and a cathode, each having an inlet and an exhaust;
   an electrolyte interposed between the anode and the cathode;
   a fuel passage in fluid communication with the anode for directing a fuel stream to and from the anode; and
   an oxidant passage in fluid communication with the cathode for directing an oxidant stream to and from the cathode; and
   a gas sensor operably associated with the fuel passage for measuring the concentration of hydrogen gas in the fuel stream, wherein the fuel passage is the anode exhaust passage, the sensor comprising a sound generator and a sound detector.

2. The fuel cell assembly of claim 1 wherein the sound generator is a transducer.

3. The fuel cell assembly of claim 2 wherein the sound generator is a piezoelectric transducer.

4. The fuel cell assembly of claim 1 wherein the sound detector is a transducer.

5. The fuel cell assembly of claim 4 wherein the sound detector is a piezoelectric transducer.

6. The fuel cell assembly of claim 4 wherein the sound generator is a transducer.

7. The fuel cell assembly of claim 1 wherein the gas sensor further comprises a temperature sensor.

8. The fuel cell assembly of claim 1 further comprising a recirculating fuel line for directing the fuel stream from the anode exhaust back to the anode inlet.

9. The fuel cell assembly of claim 8 further comprising a purge valve for directing the fuel stream to either the recirculating fuel line or the external atmosphere.

10. The fuel cell assembly of claim 8 further comprising a liquid separator in the recirculating fuel line.

11. The fuel cell assembly of claim 8 further comprising a recirculation device in the recirculating fuel line.

12. A method of operating an electrochemical fuel cell system having an anode and a cathode, the method comprising:
   directing an oxidant stream to and from the cathode;
   directing a hydrogen stream to and from the anode;
   determining the concentration of hydrogen in the hydrogen stream by:
   generating a sound in the fuel stream passage; measuring an acoustic property of the sound; and calculating the hydrogen concentration based on the measured acoustic property, wherein the hydrogen stream is the anode exhaust.

13. The method of claim 12 wherein the acoustic property is the speed of sound.

14. The method of claim 12 wherein the acoustic property is the frequency of sound.

15. The method of claim 12 wherein the electrochemical fuel cell system comprises a recirculating fuel line, the method further comprising purging the anode exhaust when the measured hydrogen concentration falls below a predetermined threshold.

* * * * *